United States Patent [19]

Fan et al.

[11] 4,322,296

[45] * Mar. 30, 1982

[54] METHOD FOR WASTEWATER TREATMENT IN FLUIDIZED BED BIOLOGICAL REACTORS

[75] Inventors: Liang-Tseng Fan, Manhattan, Kans.; Chin-Yung Wen, Morgantown, W. Va.

[73] Assignee: Kansas State Univ. Research Foundation, Manhattan, Kans.

[*] Notice: The portion of the term of this patent subsequent to Mar. 3, 1998, has been disclaimed.

[21] Appl. No.: 177,455

[22] Filed: Aug. 12, 1980

[51] Int. Cl.$^3$ .............................................. C02F 3/06
[52] U.S. Cl. .................................. 210/610; 210/618; 210/903
[58] Field of Search ...................... 210/610, 615–618, 210/661, 677, 678, 903

[56] References Cited

U.S. PATENT DOCUMENTS

| | | | |
|---|---|---|---|
| 3,347,052 | 3/1968 | Fan et al. | 210/661 X |
| 3,846,289 | 11/1974 | Jeris et al. | 210/618 X |
| 4,009,098 | 11/1974 | Jeris | 210/618 X |
| 4,009,099 | 2/1977 | Jeris | 210/618 X |
| 4,086,162 | 4/1978 | Benzaria | 210/661 |
| 4,157,959 | 6/1979 | Wen et al. | 210/661 X |
| 4,253,947 | 3/1981 | Fan et al. | 210/610 |

Primary Examiner—Thomas G. Wyse

[57] ABSTRACT

Wastewater is subjected to biological reaction in a bed containing the biological reaction bacteria on a particulate carrier wherein the lower portion of the bed is fluidized while the upper portion is maintained as a fixed bed. When the fixed bed portion becomes clogged with cellular material, the entire bed is fluidized and wash water is passed through the bed to remove excess cellular material. The method is applicable to advanced wastewater treatment, both secondary treatment for BOD removal, and tertiary treatment for nitrification and/or denitrification. The method is particularly advantageous for treatment of wastewater supplied at varying flow rates.

10 Claims, 2 Drawing Figures

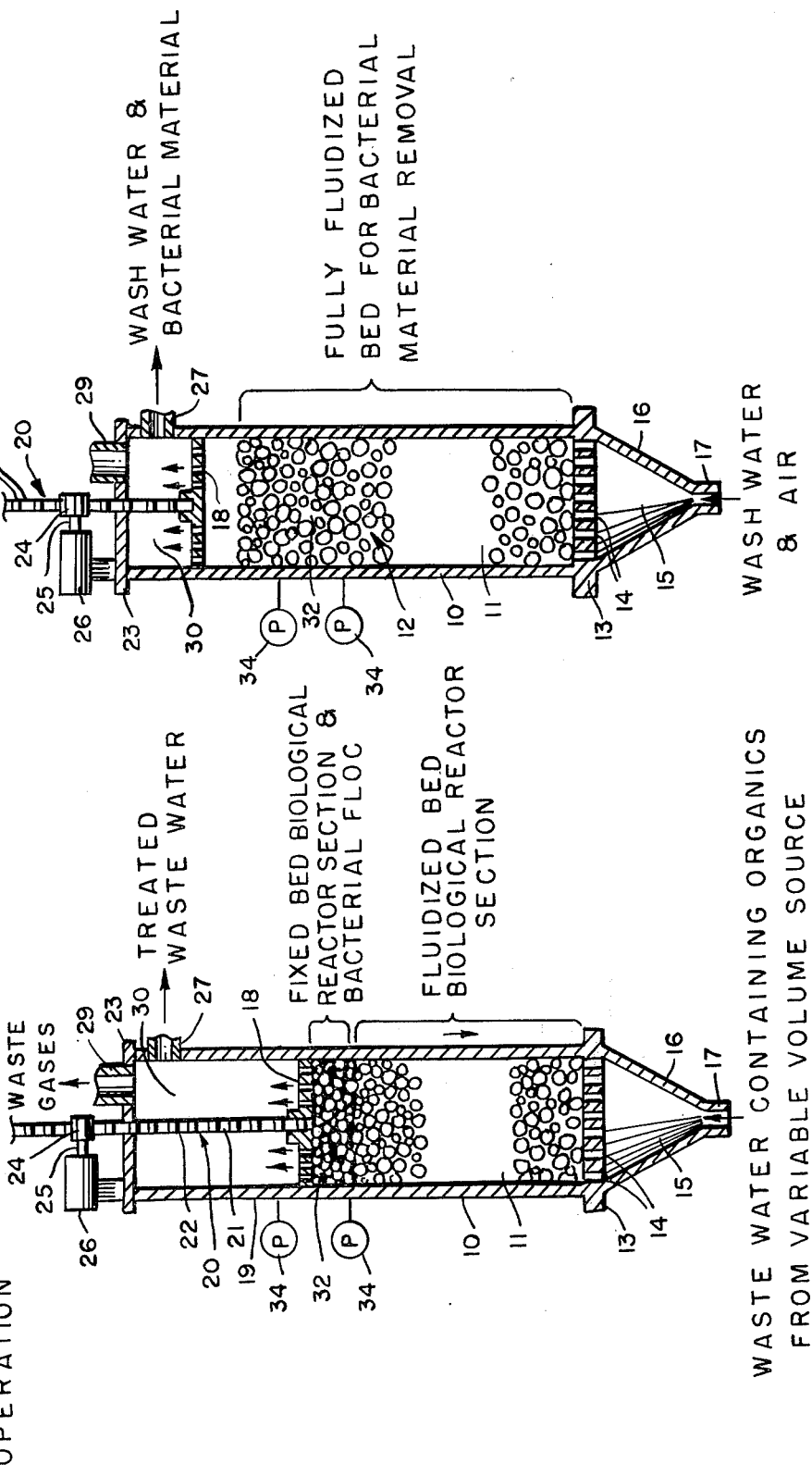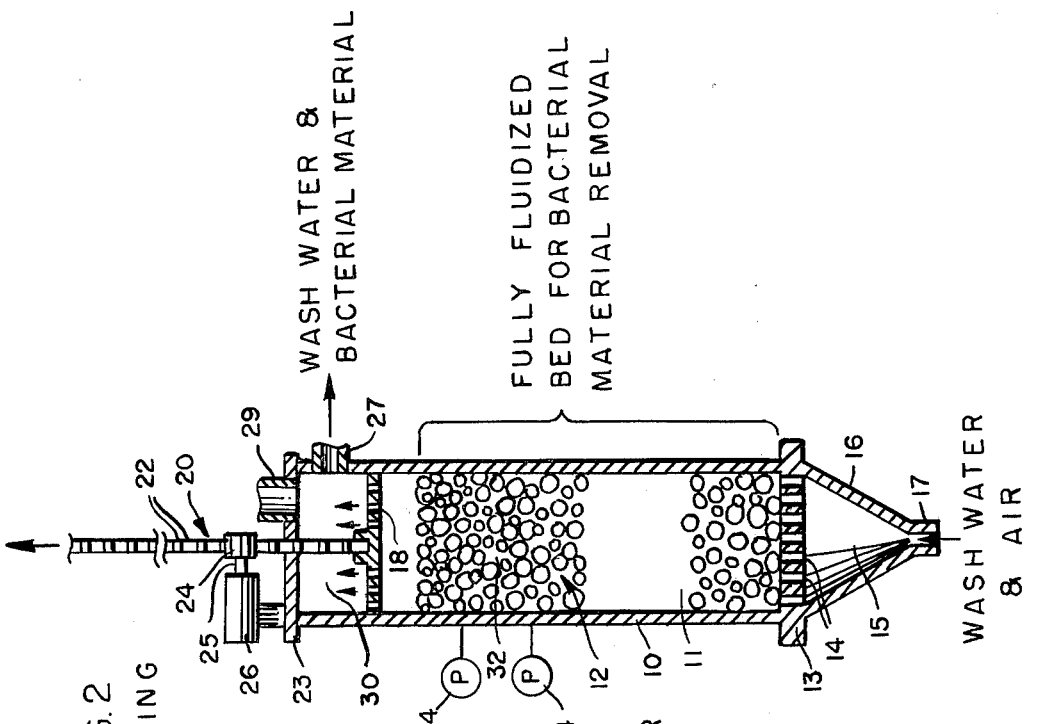

METHOD FOR WASTEWATER TREATMENT IN FLUIDIZED BED BIOLOGICAL REACTORS

BACKGROUND AND PRIOR ART

It is known that secondary treatment of wastewater for reduction of biological oxygen demand (BOD), total organic carbon (TOC), and total suspended solids (TSS) can be carried out using beds of particulate media which act as a carrier for viable bacteria performing the biological reaction. The bed may be a fixed bed, such as the sand bed of a trickling filter, or the bed may be operated in fluidized condition. The use of a fluidized bed as a biological reactor can provide a high-rate system, since extremely high concentrations of biomass (viable bacteria) can be maintained within the system. Treatment can be accomplished in less space and time which greatly reduces equipment and operating costs. One such process for fluidized bed BOD removal is described in U.S. Pat. No. 4,009,098. Comparable advantages can also be obtained for fluidized bed tertiary treatment of wastewater to remove ammonia nitrogen (nitrification), and/or to remove nitrate or nitrite (denitrification). Processes for such tertiary wastewater treatment are described in U.S. Pat. Nos. 4,009,099 and 3,846,289.

Biological fluidized bed advanced treatment of wastewater is being promoted commercially by Ecolotrol, Inc. (Bethpage, New York) and Dorr-Oliver, Inc. (Stamford, Connecticut) as the "Oxitron" biological process. It is understood that this process as applied to secondary or tertiary treatment of wastewater utilizes the teachings of the above-cited patents. According to teachings of these patents, it is important to provide means for continuous removal of excess bacterial growth during the treatment process without interrupting the process. One means proposed to accomplish this result is the provision of a mechanical agitator in the upper portion of the fluidized bed to promote the separation and removal of cellular material. The agitator, functioning as a mixer, also breaks up foam which tends to carry with it bacterial-coated media, thereby reducing but not eliminating media loss.

The loss of bacterially-coated media particles from the fluidized bed through elutriation is undesirable. It lowers active biomass concentration (MLUSS) and reduces reaction rate. With the Oxitron process, media loss occurs continually despite the operation of a mixer at the top of the fluidized bed. Therefore, for commercially practical operation of fluidized bed reactors, it has been necessary to provide solids retention tanks and solids re-entry lines to return media particles to the fluidized bed bioreactors during operation, thereby compensating for the media loss with the treated water. Despite these expedients, loss of viable bacterial cells occur to a significant extent.

Another problem encountered in such operation of bioreactors is that of periodic instability due to variations in water flow rate. The flow of wastewater is frequently subject to diurnal fluctuations over which are superimposed other erratic changes in flow rates. Thus, unstable operation may occur with considerable frequency. The result can be a channeling effect where part of the wastewater flows through the bed without being adequately treated, and/or a substantial loss of bacterial-coated media due to washout. Continual human supervision of the operation is therefore desirable.

A further limitation of fluidized bed reactors for biological wastewater treatment is that the high rate of treatment is at the expense of completeness of treatment. It is difficult to obtain as complete removal of the organic contaminants in high-rate fluidized beds as with biological treatment in the low rate non-fluidized beds of trickling filters.

SUMMARY OF INVENTION

The present invention relates to a method of carrying out a fluidized bed biological reaction for advanced treatment of wastewater in which the top of the bed is restrained with a media-retaining perforated plate to provide a smaller upper fixed bed portion and a larger fluidized bed portion therebeneath. The wastewater is subjected to initial treatment in the fluidized portion of the bed and to final treatment in the fixed portion of the bed. The media-retaining perforated plate together with the filtering action of the fixed bed portion substantially prevents media loss and greatly reduces bacteria loss. In addition, more complete removal of the organic contaminants is obtained without sacrificing the high-rate capacity of the fluidized bed.

The fixed bed section drives the reaction to completion because of the higher biomass concentration thereon. Viable bacteria cells escaping from the fluidized bed are trapped by the filtering and retention action of the fixed bed section. Further, the entering wastewater, which is high in contaminants, is first treated in a fluidized bed where intensive mixing occurs while the effluent from the fluidized portion, which is lean in contaminants, is next treated in a fixed bed where mixing is not intensive. This arrangement provides more efficient waste removal for given volume.

Preferably, the fixed bed portion is of relatively small size compared to the fluidized bed portion. The main load of waste treatment is then performed in the fluidized bed portion of the reactor, while the fixed portion complements the fluidized portion by acting as a polishing section. This provides a high rate of treatment while producing a final effluent with a much lower level of contaminants than from a comparable fluidized bed reactor.

With the operating method of this invention, stable operation is assured and a self-regulatory effect is provided. The amount of bed particles in the fixed portion of the bed is directly related to influent flow rate at a given location of the restraining plate. When the wastewater flow rate fluctuates upwardly, additional particles will tend to be shifted to the fixed portion of the bioreactor. This shift of particles can thereby provide a larger polishing section to compensate for an increased load (higher flow rate). Also, because of the increased pressure drop across the enlarged fixed bed portion, there is a tendency for the flow rate to modulate, thereby avoiding surge effects and tending to return the bed to its normal operating mode. This self-regulatory feature reduces the need for human supervision.

With the increasing flow rate, the increase in the size of the fixed bed portion also compensates for the greater load. The enlarged polishing section acts to maintain the desired level of reaction completion.

The method of this invention also facilitates cleaning of the reactor beds. Periodically, the treatment of the wastewater is discontinued and the perforated plate is raised to a level at which the bed can be fully fluidized but below a wash water outlet which is normally above the plate. Wash water is then passed upwardly through the bed at a velocity fully fluidizing the bed. The wash water is removed together with excess cellular material through the outlet, which is preferably provided in the side of the reactor. The fixed portion of the bed is broken up to release the cellular material including the bacterial floc. This may be promoted by the use of concurrent gas introduction, such as combined flow of water and air under high turbulence.

THE DRAWINGS

The method of this invention is diagrammatically illustrated in the accompanying drawing, wherein:

FIG. 1 illustrates an operation cycle in which wastewater is being treated by a biological reaction in a bed providing a smaller fixed portion above a larger fluidized portion; and FIG. 2 illustrates a cleaning cycle in which the bed is fully fluidized for removal of excess cellular material.

DETAILED DESCRIPTION

Apparatus for carrying out processes in a bed of particulate solids with the lower portion fluidized and the upper portion fixed are known and have been previously described. See Fan and Wen U.S. Pat. No. 3,374,052, granted Mar. 19, 1968; and Fan et al, *A.I.Ch.E. Journ.*, 5, 407–409 (September, 1959). The apparatus includes a vertically adjustable porous plate (usually a perforated plate) for restraining the top of the bed. When a fluid is passed upwardly through the bed at a velocity above the minimum fluidizing velocity, the restraining action of the porous plate in contact with the upper portion of the bed will create a fixed bed portion immediately beneath the plate. As the plate is lowered (at a given rate) the downward extent of the fixed bed portion will increase. Therefore, the relative size of the fluidized and fixed bed portions can be controlled. In accordance with the present invention, the top of the biological reactor bed is restrained with the perforated plate to maintain a smaller uppermost portion of the bed as a fixed bed with a larger portion of the bed therebeneath being in fluidized condition. The optimum relationship will depend on the particular biological process being carried out, the throughput rates for the wastewater, and the expected variation in flow rate. For example, the fixed bed section may have a vertical extent of as little as 0.05 to as much as 1.0 meter while the fluidized bed section has a vertical extent of from 0.5 to 5.0 meters.

The method of the present invention is applicable to all processes for advanced wastewater treatment by biological reaction. Where the process requires aerobic bacterial growth, air or oxygen can be added to the wastewater in accordance with known practices. Where the desired reaction is promoted by the addition of a nutrient, such as a carbon source for denitrification, this can also be added to the water in accordance with prior practice. In general, the biological reactor is operated in the same manner as prior art fluidized bed biological reactors, except that the upper portion of the bed is restrained by a perforated plate to create the fixed bed portion. Examples of such processes and processing apparatus are described in U.S. Pat. Nos. 3,846,289, 4,009,098 and 4,009,099. As distinguished from the processes described in those patents, however, it is not desirable during the biological reaction treatment to operate an agitator or mixer at the top of the fluidized bed, or to remove and return carrier particles during the biological treatment. The perforated plate is provided with perforations of smaller size than the size of the particulate carrier so that it retains the carrier in the treatment zone.

The media employed as the carrier for the bacterial growth can be the same media as previously employed in fluidized bed biological reactors. Sand which has been sized to obtain the desired particle size is particularly suitable. Other useable particulate carriers include coal, carbon, alumina, plastic particles, etc. The specific gravity of the particles is not critical, but must be greater than that of water. For example, the media may have an average particle size of from about 1.0 to 20 mm. in diameter, and of a specific gravity of about 1.05 to 3.0. Preferably, the media has been sized to eliminate fines which would pass through the openings in the perforated plate, or such fines are washed out of the media during the initial fluidization and start-up of the biological reactor.

In accordance with known practice, the carrier in the reactor is inoculated with bacteria of the kind needed for the desired biological reaction. Since such bacteria are frequently present in sewage or wastewater, such natural sources can be used for the seeding, as well as cultured inoculants.

For treating the water containing organic material to reduce its biochemical oxygen demand, appropriate bacteria are used which convert organic carbon and/or BOD into carbon dioxide gas and/or cellular material. In general, the carrier will be seeded with bacteria adapted to feed on wastewater such as aerobic or facultative bacteria. The subgenus of heterotrophic biota have been particularly used for this purpose, including biota naturally found in sewage, such as pseudomonas, bacillus, and/or alcaligenes. Such biological reaction treatment of wastewater is usually referred to as secondary treatment, since it follows a primary non-bacteriological treatment. Further treatment of wastewater, usually referred to as tertiary treatment, involves denitrification, which converts nitrate or nitrite to nitrogen. Denitrification, as such, does not remove ammonia or amine nitrogen, but nitrification by bacterial reaction may be used to convert the ammonia or amine nitrogen to nitrate, which can then be removed by denitrification.

Nitrification is carried out under aerobic conditions, as is BOD removal, but a separate treatment is required because the bacteria are different. The bacteria are selected to convert ammonia nitrogen to oxidized forms of nitrogen (nitrate or nitrite). Nitrosomonas and nitrobacter, which are naturally found in municipal wastewater, are particularly suitable for this purpose. The denitrification reaction is carried out under anaerobic conditions with addition of a carbon source, which is commonly methanol. Common denitrifying bacteria are used, such as pseudomonas, bacillus, and/or micrococcus.

Once the bacterial growth has been established in the bed for the desired biological reaction, the treatment of the wastewater may be carried out continuously. The wastewater is passed upwardly through the bed at a velocity at least sufficient to fluidize the bed. In practice, velocities considerably in excess of the minimum fluidizing velocity will be desirable, such as velocities from 1.2 to 6 times the minimum fluidizing velocity will be desirable. The size of the upper fixed bed portion will be determined in relation to the expected average flow rate and the variation therefrom. At the lowest flow rate, part of the bed should still be in fixed condition, while at the highest flow rate, the fixed bed should still be of smaller size than the fluidized bed portion. The treated water passes outwardly through the perforations in the restraining plate while the media is substantially retained because the perforations are of smaller size than that of the media particles. The treated water is removed from an outlet located above the perforated plate. With a vessel of cylindrical cross section the perforated plate will have a diameter corresponding to the internal diameter of the reaction vessel, and will be mounted so that it can be raised and lowered within the upper portion of the reaction vessel. For reasons which will subsequently be further discussed, it is desirable to provide a side outlet in the wall of the vessel located above the perforated plate when it is at a level restraining the bed and creating the upper fixed bed portion. Since gas is evolved in most of the bacteriological processes of water treatment, a vent for waste gases should be provided, which conveniently will usually be located in the top of the reaction vessel, or at least above the level of the water outlet.

As the treatment cycle proceeds, the fixed bed portion will act as a filter for the flocculated or aggregated bacterial cells. Individual bacterial cells could pass through the fixed bed portion, but most of the bacterial growth is either on the surface of the carrier particles or in the form of bacterial floc, which is retained within or at the bottom of the fixed bed portion. The wastewater is continued to be passed through the bed for initial biological reaction in the fluidized bed portion and final biological reaction in the fixed bed portion until the fixed bed portion becomes so clogged with cellular material that there is an excess pressure drop thereacross. The extent of the accumulation can be monitored by pressure observations. Automatic recording instrumentation may be used for this purpose.

When the fixed bed portion has become plugged with the cellular material, a cleaning cycle is instituted. The treatment of the wastewater is temporarily discontinued and the perforated plate is raised to a level at which the bed can be fully fluidized. Preferably, the plate is out of contact with the top of the expanded fluidized bed. However, the plate may be at a level below the wash water outlet so that the removed excess cellular material passes through the plate and into the outlet. For this purpose, wash water is passed upwardly through the bed at a velocity sufficient to fully fluidize the bed while removing the wash water together with excess cellular material through the side outlet. As part of the washing or cleaning operation, it is important that the fixed portion of the bed be broken up and fluidized to release cellular material therefrom. The introduction of a gas such as air provides an increased turbulence and scouring action which assists the breaking up and fluidizing of the fixed bed portion and the removal of the bacterial material therefrom. By using plate perforations of sufficiently large size and bed particles sized for retention by the plate the media can be retained while removing the separated bacterial particles. With the full fluidization of the bed, the circulating particles of media within the bed will tend to exert a shearing or abrasion action on each other.

The method of operation of this invention with respect to the operating cycle has particular advantage where the wastewater being treated substantially varies in flow rate. For example, under frequently encountered conditions with respect to variation in volume of wastewater requiring treatment, the variation may be by a factor of at least 5% up to as much as 25%, from the average flow rate on a daily-24 hour basis. While variations of such extent may not occur during every day of operation, they can be expected to occur frequently, and therefore the self-compensating action of the method of this invention provides important advantages. As described above, for a given location of the restraining plate, increases in flow rate will tend to increase the size and downward extent of the fixed bed section, while decreases in flow rate will tend to decrease the size and downward extent of the fixed bed section, the fluidized bed section being correspondingly increased or decreased in size.

The method of the present invention will be further illustrated in connection with certain examples.

EXAMPLES

An apparatus which may be used for practicing the present invention is illustrated in the accompanying drawing. The apparatus is similar to the one disclosed in U.S. Pat. No. 3,374,052. It includes a vertically-extending cylindrical column 10 which provides a cylindrical interior space 11 for receiving the particulate carrier 12. At the bottom of the space 11 there is provided a distributor plate 13 having a plurality of liquid inlet ports 14. Ports 14 are preferably distributed in a uniform pattern in all directions across the distributor plate. The ports may be circular in cross section and should have a diameter smaller than the diameter of the particles of carrier 12. Plate 13 serves as a fluidizing inlet for the wastewater to be treated. Distribution nozzles or spouted fluidized bed inlets may be used instead of a distributor plate.

An enclosed chamber 15 is provided below distributor plate 13. The wall 16 of the chamber may have a conical shape, thereby functioning as a conical-shaped flow regulator. The lower end of chamber 15 is connected to a liquid inlet conduit 17, which receives the wastewater from a pump or other pressurizing source of supply.

Above bed 12, there is provided a sieve plate 18 (or other perforated plate means) for restraining the upper surface of the bed. Plate 18 is provided with a multiplicity of perforations 19, which are preferably distributed over the entire surface thereof. Means are provided for selectively raising and lowering plate 18. In the illustration given, and as more particularly described in U.S. Pat. No. 3,374,052, the lower end of a vertically-extending rack bar 20 is connected to the center of plate 18 by means of a sleeve 21. Bar 20 and the opening within sleeve 21 may conveniently be of square or rectangular cross-section, and bar 20 is provided with teeth 22 on at least one side thereof. The upper end of column 10 is closed by a cover plate 23, and rack bar 20 projects upwardly beyond cover 23 through a central opening therein. A driving mechanism is connected to the upper portion of bar 20, including pinion 24 provided with teeth engaging the teeth of rack 20, and the pinion is driven by a shaft 25 connected to an electric motor 26. Suitable controls (not shown) may be provided for operating motor 26, either manually or automatically.

An outlet conduit 27 extends through an opening in the upper portion of the wall of column 10. The side outlet 27 may be adjacent to or spaced downwardly from cover 23. Both the normal operating position and the wash position of plate 18 are below outlet 27, as shown in FIGS. 1 and 2.

To facilitate the venting of waste gases separately from the treated water, a gas vent or stack 29 may be provided on top of the reactor, communicating with the freeboard space 30 through an opening in cover 23.

During the cleaning cycle, a gas such as air may be introduced into the bed, either separately or together with the wash water. Combined air-water introduction is illustrated in FIG. 2. A high degree of turbulence and abrasive action can thereby be provided. The media particles will scour themselves with the release of bacterial material. Further, the abrasive, scouring action of the bed will reduce the particle size of the released bacterial floc so that it can pass through plate 18 in particulate form.

To permit pressure conditions within bed 12, and particularly across the fixed bed portion thereof to be monitored, a series of pressure gauges 34 may be provided in vertically-spaced relation on the outside of column 11, being connected to suitable pressure taps extending through the side wall of the column. Only two pressure gauges are shown, but it will be understood that additional gauges, or pressure sensing taps may be provided. Gauges may be designed for manual observation, but it will be understood that in automated versions of the apparatus, pressure sensing recording apparatus may be employed.

In a specific example, the particulate carrier 12 may consist of sized and grated coal particles (silica) having a size range of from 6 to 12 mm. Correspondingly, fluidizing openings 14 and plate 13 and the perforations 19 in plate 18 will have a diameter small enough to retain the particulate carrier, such as 5.0 mm.

Preparatory to the treating of the wastewater, the carrier 12 is seeded with the appropriate bacteria for BOD removal. For example, the heterotrophic bacteria associated with common sewage can be used, oxygen being introduced during the seeding and added to the wastewater during treatment. Where the desired reaction is the removal of ammonic nitrogen, the reactor is seeded with nitrosomons and/or nitrobacter, and the seeding and treatment of the wastewater are carried out under aerobic conditions with the addition of oxygen. For denitrification, anaerobic conditions are used. The carrier may be seeded with bacteria associated with common sewage, such as pseudomonas, bacillus, etc. Methanol may be added to the water being treated as a carbon source to promote the denitrification.

Bacterial growth is established on the surfaces of the carrier particles, the particulate carrier serving as a support for the biomass. Once established, the bacteria will grow profusely.

To start the treatment operation, sieve plate 18 is lowered into contact with the top of bed 12. For example, the position of plate 18 may be selected in relation to the fluidizing flow rate of the wastewater introduced under pump pressure through conduit 17 so that approximately 5% of the vertical height of bed 12 comprises an upper fixed bed, and approximately 95% of the vertical height of the bed comprises the fluidized bed section. It will be understood that the relative size of the fixed bed and fluidized bed sections can be varied. However, there should be sufficient fixed bed to carry out a finishing treatment of the wastewater so that the organic contaminant being removed by the bacterial reaction is reduced to a level of substantial completion.

Once stable operating conditions are achieved, the incoming wastewater is subjected to high rate treatment in the fluidized bed section. The partially treated water of reduced organic content is subjected to a finishing reaction in the fixed bed section where the concentration of the reaction bacteria is higher. Aggregated or flocculated bacteria are caught by the fixed bed section, the bed having a filtering action on the larger masses of bacteria. At the same time, the bacteria-coated particles of carrier are retained within the reactor, since they are of larger diameter than the plate perforations and are thereby retained within the fixed bed section. Loss of bacterial cells through plate 18 will also be minimal. The treated water passes into the space above plate 18 and exits through the side outlet 27. Waste gases, such as those produced by the biological reaction, collect in the freeboard space 30 above the liquid level and are exhausted through outlet 29.

The operational cycle is continued until the fixed bed section of the reactor becomes so clogged with cellular material that the pressure drop across the fixed bed section is excessive. At that stage, bacterial floc will have collected at the bottom of the fixed bed section. This floc must be removed together with excess cellular material from within the fixed bed. The apparatus is then converted to the cleaning cycle, as illustrated in FIG. 2.

For the cleaning cycle, plate 18 is withdrawn toward the top of column 10 being positioned, as shown, just below outlet 27. Wash water and air are introduced under pump pressure through inlet 17. Higher fluidizing velocity will be used for the washing than for the treating operation. For example, if a fluidizing velocity of three times the minimal fluidizing velocity is used for the treating operation, a fluidizing velocity of five to six times or more the minimum fluidizing velocity may be used for the washing operation.

Once the bed 12 is fully fluidized, as the accumulated cellular material is broken up, it flows out with the wash water through the plate 18 and the outlet 27. The fluidization of the particles which were retained as a fixed bed during the operational cycle will subject these particles to an abrading or shearing action to which the particles tend to scour their own surfaces by mutual contact. This action will liberate additional amounts of the excess cellular material.

For the next and subsequent operating cycles, the reactor can be started up more quickly than in the initial operating cycle, since the bacterial growth has already been established on the carrier. The sieve plate 18 is returned to the position at which it will maintain the desired fixed bed section, and the treatment is carried out as previously described with reference to FIG. 1.

The advantages of the method of this invention over prior art fluidized bed biodigesters can be summarized as follows:

(1) The loss of microorganism-coated media particles by elutration is greatly reduced, and the need for a solids retention tank and solids re-entry lines are eliminated. The filtering property of the fixed bed portion of the bioreactor prevents the media particles from escaping during normal operating, and the media particles are also retained during washing by the action of the sieve plate.

(2) More stable operating conditions are provided, and this is particularly important for there are substantial variations in the infruant flowrate. Channeling effects through the bed are eliminated, and a self-regulatory action is provided. The amount of bed particles in the fluidized and fixed portions of the bed is directly related to the infruant flowrate. When the waste water flowrate fluctuates upwardly, additional particles are shifted to the fixed portion of the bioreactor, thereby providing a larger polishing section which compensates for the increased load to the bioreactor. Further, the increased pressure drop across the fixed bed portion will cause the flowrate to decrease, thereby tending to return the bed to a normal operating mode.

(3) Entering waste, which is high in contaminants, is first treated in the fluidized portion of the reactor where intensive mixing occurs, while the effluent from the fluidized portion which is lean in contaminants, is treated in the fixed bed where mixing is not intensive. This arrangement gives a highly efficient waste removal for a given volume.

(4) Filtration by the fixed bed section of the bioreactor retains bacteria cells and prevents these from being lost to the reactor. This adds to the effectiveness of the bioreactor.

(5) With prior art fluidized beds, high velocity wash water with resulting turbulence, or mixtures of wash water and gas creating highly turbulent conditions, could not be employed without large losses of the media, which must be recovered and returned to the bioreactor. With the method of the present invention, however, the bed may be washed at high velocity with resulting improved abrasion, scouring, and separation of the bacterial floc and excess bacterial coating on the media in a fine enough particulate form to pass outwardly through the sieve plate.

We claim:

1. The method of carrying out a fluidized bed biological reaction for advanced treatment of wastewater, in which there is provided within a confined upwardly-extending treatment zone an upflow bed of solid particulate carrier having the biological reaction bacteria cells growing thereon, said wastewater to be treated being passed upwardly through said bed at a velocity at least sufficient to fluidize said bed; wherein the improvement comprises:
   (a) restraining the top of said bed with a perforated plate to maintain a smaller uppermost portion of said bed as a fixed bed with a larger portion of said bed therebeneath being in fluidized condition, the perforations in said plate being of smaller size than said carrier so as to retain said carrier in said treatment zone while permitting the treated water to pass therethrough;
   (b) continuing to pass the wastewater to be treated through said bed for initial biological reaction in said fluidized bed portion and final biological reaction in said fixed bed portion until said fixed bed portion has become clogged with cellular material;
   (c) discontinuing said treatment and raising said plate to a level at which said bed can be fully fluidized but below a wash water outlet from said confined space; and
   (d) passing wash water upwardly through said bed at a velocity sufficient to fully fluidize said bed while removing wash water together with excess cellular material through said plate and into said outlet, the fixed portion of said bed being broken up and fluidized to release cellular material therefrom.

2. The method of claim 1 in which the flow rate of said wastewater being treated varies substantially, said variation being by a factor of at least 5% with reference to the average daily (24 hrs) flow rate.

3. The method of claim 1 in which said biological reaction is for removal of biochemical oxygen demand (BOD) and is carried out under aerobic conditions by addition of air or oxygen to said wastewater being treated.

4. The method of claim 1 in which said biological reaction is for removing ammonia nitrogen and is carried out under aerobic conditions by addition of air or oxygen to said wastewater being treated.

5. The method of claim 1 in which said biological reaction is for denitrification and is carried out under anaerobic conditions with addition of a carbon source to said wastewater being treated.

6. The method of carrying out a fluidized bed biological reaction for advanced treatment of wastewater, in which there is provided within a confined upwardly-extending treatment zone an upflow bed of solid particulate carrier having the biological reaction bacteria cells growing thereon, said wastewater to be treated being passed upwardly through said bed at a velocity at least sufficient to fluidize said bed; wherein the improvement comprises:
   (a) passing said wastewater upwardly through said bed at an upward velocity greater than the minimum fluidization velocity for said bed when unrestrained;
   (b) restraining the upper surface of said bed with a perforated plate to maintain a smaller uppermost portion of said bed as a fixed bed with a larger portion of said bed therebeneath being in fluidized condition, said upper fixed bed portion being of relatively small size compared to said fluidized bed portion, the perforations in said plate being of smaller size than said carrier so as to retain said carrier in said treatment zone while permitting the treated water to pass therethrough;
   (c) continuing to pass the water to be treated through said bed for initial biological reaction in said fluidized bed portion and final biological reaction in said fixed bed portion until said fixed bed portion has become clogged with cellular material, said water being treated varying substantially in flow rate, said variation being by a factor of at least 5% with reference to the average daily (24 hrs) flow rate, said fixed bed portion increasing in size and downward extent when said water flow rate substantially increases;
   (d) discontinuing said treatment and raising said plate to a level at which said bed can be fully fluidized but below a wash water outlet from said confined space; and
   (e) concurrently passing a gas and wash water upwardly through said bed at velocities sufficient to fully fluidize said bed while removing wash water together with excess cellular material through said plate and into said outlet, the fixed portion of said bed being broken up and fluidized to release cellular material therefrom.

7. The method of claim 6 in which said biological reaction is for removal of biochemical oxygen demand (BOD) and is carried out under aerobic conditions by addition of air or oxygen to said wastewater being treated.

8. The method of claim 6 in which said biological reaction is for removing ammonia nitrogen and is carried out under aerobic conditions by addition of air or oxygen to said wastewater being treated.

9. The method of claim 6 in which said biological reaction is for denitrification and is carried out under anaerobic conditions with addition of a carbon source to said wastewater being treated.

10. The method of claim 6 in which said gas passed with said wash water is air.

* * * * *